United States Patent [19]

Berger et al.

[11] Patent Number: 5,440,033

[45] Date of Patent: Aug. 8, 1995

[54] INDOLYL-, PYRROLYL- AND PYRAZOLYL SUBSTITUTED BENZAZEPINES

[75] Inventors: Joel G. Berger, Cedar Grove; Joseph A. Kozlowski, Plainsboro; Wei Chang, Livingston, all of N.J.

[73] Assignee: Schering Corporation, Kenilworth, N.J.

[21] Appl. No.: 149,411

[22] Filed: Nov. 9, 1993

[51] Int. Cl.$^6$ .................. C07D 403/04; A61K 31/55
[52] U.S. Cl. ..................................... 540/549; 514/213
[58] Field of Search ......................................... 540/594

[56] References Cited

U.S. PATENT DOCUMENTS 5,015,639  5/1991  Berger et al. .................. 540/549

*Primary Examiner*—Robert T. Bond
*Attorney, Agent, or Firm*—James R. Nelson; Eric S. Dicker; Matthew Boxer

[57] ABSTRACT

Disclosed herein are compounds of the formula

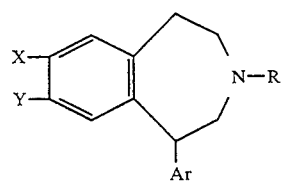

and pharmaceutically acceptable salts thereof, wherein Ar, R, X, and Y are as described herein are described. The compounds are useful for treating psychoses and depression and for providing analgesia. Compositions containing the compounds and methods for producing the compounds are also disclosed.

6 Claims, No Drawings

INDOLYL-, PYRROLYL- AND PYRAZOLYL SUBSTITUTED BENZAZEPINES

BACKGROUND OF THE INVENTION

This invention relates to 5-substituted -2,3,4,5-tetrahydro-1H-3-benzazepines, their preparation and pharmaceutical compositions containing them. The compounds have valuable pharmaceutical properties in the treatment of psychoses, depression, pain, hypertension, schizophrenia and drug dependence. Additionally, the compounds have antihistaminic, anticholinergic, antiaggressive and general tranquilizing properties. 1- and 5-substituted 2,3,4,5-tetrahydro-1H-3-benzazepines are described in publications, for example, U.S. Pat. No. 5,015,639 (Berger, et al.). The activities discussed include anti-bacterial effects, central nervous system effects, and hypotensive effects.

SUMMARY OF THE INVENTION

The invention relates to compounds of the formula:

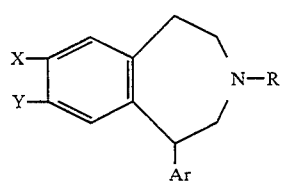

and pharmaceutically acceptable salts thereof,
wherein Ar is selected from the group consisting of

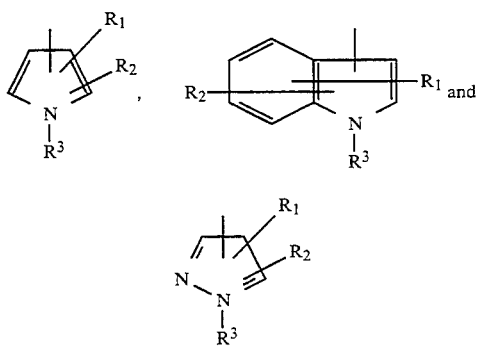

$R$, $R_1$, $R_2$ and $R_3$ are each independently hydrogen or lower alkyl with the proviso that when Ar is

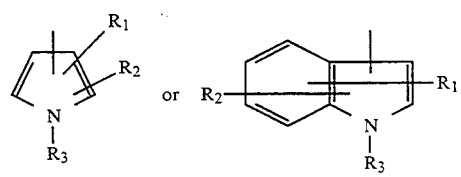

$R_1$ and $R_2$ cannot both be hydrogen;
X is hydrogen, halogen, lower alkyl or $-CF_3$; and

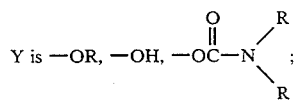

wherein each R is independently as described above.

Substituted indolyl, pyrrolyl and pyrazolyl, wherein the substituents are R, $R_1$ and $R_2$, may be represented generally by the formulas:

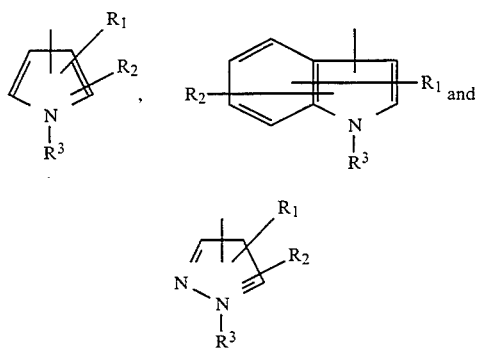

Attachment to the benzazepine nucleus at all positions on the Ar moiety is contemplated. Thus, Ar is intended to include the following structures:

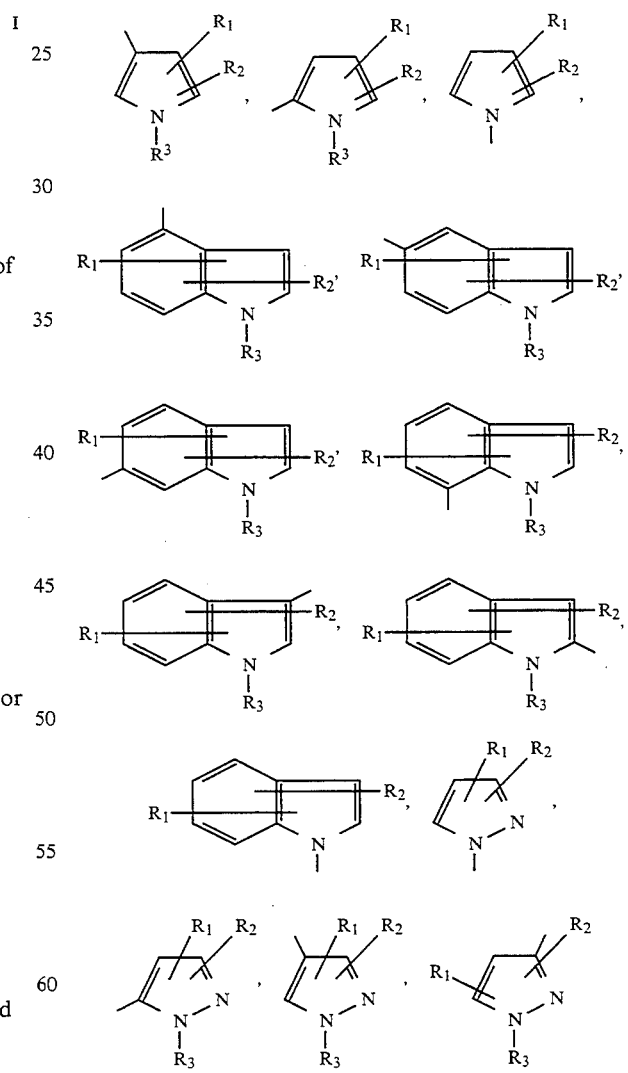

The benzazepine ring of formula I contains a chiral carbon atom at the 5-position, making two stereo isomers of each compound of formula I possible. All such stereo isomers and mixtures thereof are within the scope of this invention. Furthermore, any further stereoisomers caused by chiral carbon atoms in Ar are also intended to be part of this invention.

Preferred compounds of formula I are those wherein X is halo (more preferably chloro), Y is hydroxy, Ar is substituted pyrrolyl and each R, $R_1$, $R_2$ and $R_3$ is independently hydrogen or methyl. Four particularly preferred specific compounds of formula I are those wherein X is chloro, Y is hydroxy, R is methyl and Ar is

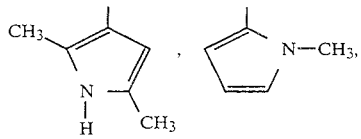

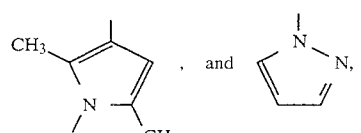
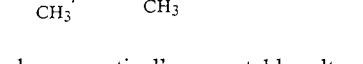

and the pharmaceutically acceptable salts of the foregoing. In another of its aspects, the present invention provides a process for the preparation of a compound of the formula I.

Exemplary compounds of the invention are as follows:

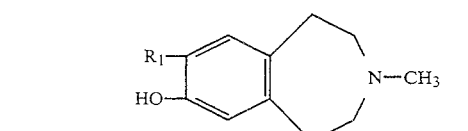

| Compound | $R_1$ | R |
|---|---|---|
| A | Cl | 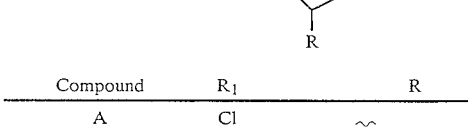 |
| B | $CH_3$ |  |
| (±)C | Cl | 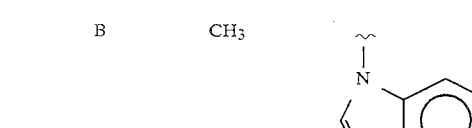 |
| (+)D | Cl | 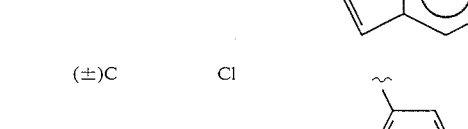 |

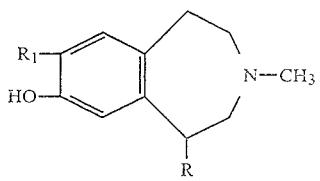

| Compound | $R_1$ | R |
|---|---|---|
| (−)E | Cl | 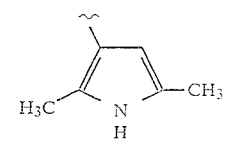 |
| F | Cl | 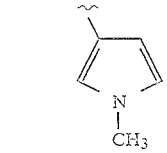 |
| G | Cl | (similar pyrrolyl with N-$CH_3$) |
| H | Cl | 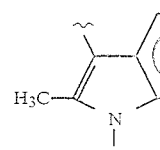 |
| I | Cl | (pyrazolyl) |
| J | Cl | 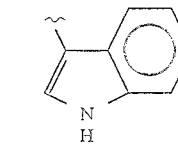 |
| K | Cl | 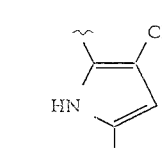 |
| L | Cl | (dimethylpyrrolyl HN) |

-continued

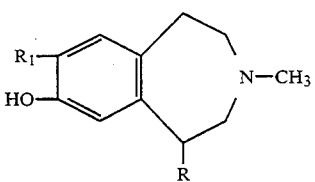

| Compound | R₁ | R |
|---|---|---|
| M | Cl | 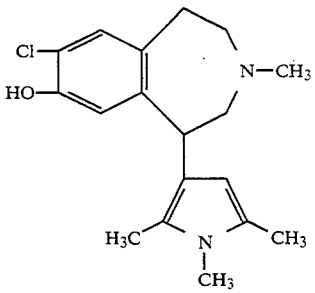 |

The most preferred compound of the invention is

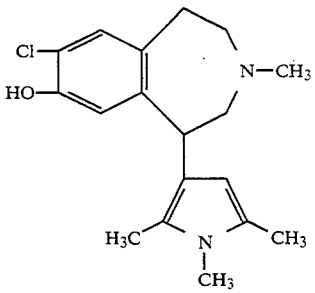

or a pharmaceutically acceptable salt thereof.

The compounds of formula I possess analgesic, anticholinergic, antiaggressive and general tranquilizing properties. The invention therefore includes pharmaceutical compositions comprising a compound of formula I in combination with a pharmaceutically acceptable carrier and methods for treating mental disorders including psychoses, schizophrenia or depression in a mammal, or for the control of pain or anxiety in a mammal by administering an effective amount of a compound of formula I to the affected mammals.

DETAILED DESCRIPTION OF THE INVENTION

Certain compounds of this invention may exist in isomeric forms. The invention contemplates all such isomers both in pure form and in admixture, including racemic mixtures.

Compounds of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of this invention.

Certain compounds of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium biocarbonate. The free base forms differ from their respective salt forms somewhat in certain physical properties, such as solubility in polar solvents, but the salts are otherwise equivalent to their respective free base forms for purposes of the invention.

When utilized herein and in the appended claims, the following terms, unless otherwise specified, have the following scope:

halo represents fluoro, chloro, bromo or iodo;

lower alkyl represents straight or branched carbon chains having 1 to 6 carbon atoms aryl is unsubstituted phenyl or substituted phenyl;

substituted phenyl is phenyl mono- or di-substituted by lower alkyl, hydroxy, lower alkoxy, lower alkylthio, halo, trifluoromethyl, or combinations thereof;

aryl lower alkyl is lower alkyl as described above, wherein one of the hydrogens is replaced by aryl as described above.

In another of its aspects, the present invention provides a process for the preparation of a compound of the formula I. selected from the following processes A to E:

A: reduction of a carbonyl compound of the formula:

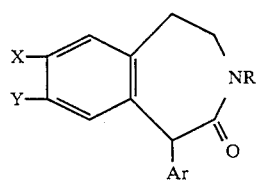

II

B: reduction of an ester of the formula:

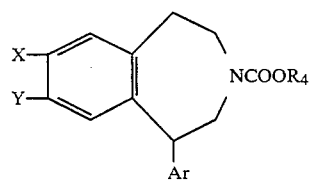

III

C: reduction at the double bond of a salt of the formula:

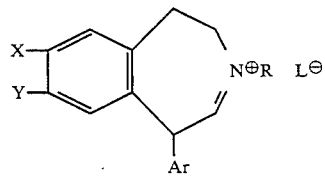

IV

D: intramolecular cyclization of a compound of the formula:

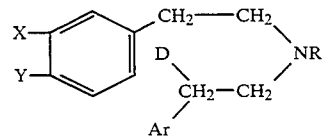

V with elimination of HD and formation of the azepine ring, and

E: reduction at the olefinic double bond of a compound of the formula:

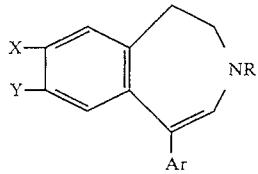

VI wherein in the foregoing formulae X, Y, R and Ar are as defined for formula I, $R_4$ is lower alkyl, aryl, or aryl lower alkyl; L is an anion, preferably an anion derived from a halo acid or a sulfonic acid, and D is a reactive group OH capable of being eliminated as DH with formation of the azepine ring.

The process may be followed if desired by one or more of the following optional steps:

(i) removal of any protecting group present at a nitrogen atom, (ii) alkylation at a nitrogen atom wherein R is hydrogen to introduce R representing alkyl, (iii) esterification of Y where Y is —OH, (iv) halogenation of X wherein X is —H, (v) hydroxymethylation of X wherein X is —H, following by reduction of the so-introduced hydroxymethyl group to methyl.

The compounds of formula I may be prepared by process A to E, described in general terms previously and more specifically below.

Process A

Compounds of formula II may be prepared by processes analogous to previously known steps of U.S. Pat. No. 5,015,639, columns 7 to 11. Of course, the group

of that patent is replaced with

to produce compounds of the present invention. Alternatively, the group Ar can be introduced by the reaction

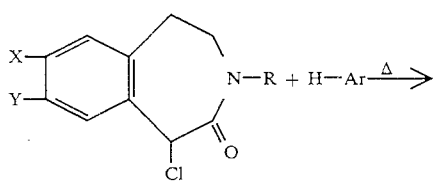

as shown in U.S. Pat. No. 5,015,639 which is hereby incorporated by reference.

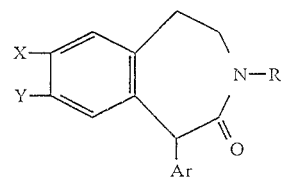

A Compound II of the formula shown just above is then reduced to a compound of formula I by reaction with a suitable reducing agent to reduce the carbonyl oxygen. Suitable reducing agents include $BH_3/THF$, $LiAlH_4$, $NaBH_4$/pyridine, $NaAlH_2$ $(OCH_2CH_2OC_2H_5)_2$, etc. The reduction may be carried out at any suitable temperature, e.g., from about 0° C. to about 120° C. and may be performed in an inert solvent such as THF, ether, and the like.

Process B

Compounds of formula III may be prepared by processes analogous to those shown in U.S. Pat. No. 5,105,639, columns 11 to 14, again introducing the

groups of the present invention in place of the

groups shown in the patent.

Reduction of an ester of formula III to a compound of formula I wherein $R_3$ is $CH_3$ can be performed by reaction with any suitable reducing agent, e.g., $LiAlH_4$, etc. in a suitable solvent such as ether, THF, and the like, at a temperature range of about 0° C. to the reflux temperature of the reaction mixture. If $R_4$ is not in accordance with the desired R group, may be replaced by reacting the reduced compound with H—R.

Process C

Compounds of formula IV can be prepared as shown in U.S. Pat. No. 5,015,639, columns 14 and 15, again substituting the groups

for the groups

Compounds of formula IV are converted to compounds of formula I by reaction with a suitable hydrogenating agent such as $NaBH_4$ in a solvent such as a lower alcohol at temperatures from about 0° C. up to the reflux temperature of the reaction mixture.

Process D

Compounds of formula V may be prepared as shown in U.S. Pat. No. 5,015,639, column 15 and 16. In formula V reactive group D is preferably hydroxy, alkoxy, halogen, a sulfonic acid ester, e.g., -o-tosyl or -o-mesyl. The condensation reaction takes place by treating a compound of formula V with a strong acid such as HCl or CF₃SO₃H in an inert medium such as methylene chloride or nitrobenzene at temperature of from about 0° C. to the reflux temperature of the reaction mixture.

Process E

Process E is analogous to the reaction given in U.S. Pat. No. 5,015,639 at column 31, step C.

In all of the above processes it may be necessary to protect certain groups on the raw materials or intermediates. Use of such protecting groups is well known to those skilled in the art, who will also know how to isolate pure compounds of formula I, if desired.

The starting materials in all of the above processes are known or may be prepared by known methods.

The utility of the compounds of formula I may be demonstrated by test procedures designed to indicate their anti-psychotic and anti-depressive activity.

CONDITIONED AVOIDANCE SUPPRESSION IN RATS

Clinically active antipsychotic drugs are known to depress discrete trial avoidance behavior at doses that do not retard escape response #Ann. N.Y. Acad. Sci. 66, 740 (1957). A series of experiments was carried out to assess the ability of the compounds of this invention to suppress the conditioned avoidance response (CAR) in rats.

Materials and Methods

Rats were required to jump onto a platform located 6.75 inches (17.15 cm) above the grid floor of an experimental chamber in response to a 5-second tone to avoid a 10-second foot shock (0.6 ma). Each experimental session consisted of 20 such trials presented at 30-second intervals. A correct CAR is scored whenever the rat jumps onto the platform during the tone (prior to foot shock). An escape response is scored when the rat jumps onto the platform during a shock. A response failure is defined as the lack of an escape response during the 10-second shock period.

Groups of 6–8 rats were trained in two consecutive days (total of 40 trials). Rats that reached criterion on day 2 (correct CARs on 16 or more of the 20 trials) were treated with either a test drug or vehicle on day 3. Suppression of CAR was analyzed statistically using Student's t-test comparing the performances of drug-treated to vehicle-treated rats. The minimal effective dose (MED) for each drug is defined as the lowest dose tested that significantly ($P<0.05$) reduced avoidance responding.

Results

Representative compounds of the invention when tested by the above procedure manifested a dose-related specific blockade of conditioned avoidance response as set forth in Table 1 below:

TABLE 1

| Compound | $R_1$ | R | $K_i$, nm D1 | $K_i$, nm D2 | NA = not active Rat CAR (mpk @ 1 h) |
|---|---|---|---|---|---|
| A | Cl | (N-indolyl) | 26 | >10,000 | No data |
| B | CH₃ | (N-indolyl) | 607 | IC₅₀ > 10 mm | No data |
| (±)C | Cl | (2,5-dimethylpyrrolyl) | 2.8 | 2451 | 10, 50 @ 6 h. (1.5 po @ 6 h. monkey) |
| (+)D | (Cl | (2,5-dimethylpyrrolyl) | 0.54 | 590 | 10 (tremors at 30 po) |

TABLE 1-continued

| Compound | R₁ | R | $K_i$, nm D1 | $K_i$, nm D2 | NA = not active Rat CAR (mpk @ 1 h) |
|---|---|---|---|---|---|
| (−)E | Cl | 2,5-dimethyl-1H-pyrrol-3-yl | 41 | 613 | NA 30 |
| F | Cl | 1-methyl-1H-pyrrol-2-yl | 41 | 10,000 | NA 30 |
| G | Cl | 1,2,5-trimethyl-1H-pyrrol-3-yl | 2.8 | 383 | 10 (5 mpk @ 4 h monkey) |
| H | Cl | 1-methyl-1H-pyrrol-3-yl | 2.2 | 177 | No data |
| I | Cl | 1H-pyrazol-4-yl | 12 | >10,000 | No data |
| J | Cl | 2-methyl-1H-indol-3-yl | 127.3 | >10,000 | NA po or s.c. |
| K | Cl | 1H-indol-3-yl | 55.2 | >10,000 | NA po or s.c. |
| L | Cl | 2,4-dimethyl-1H-pyrrol-? | | | No data |

TABLE 1-continued

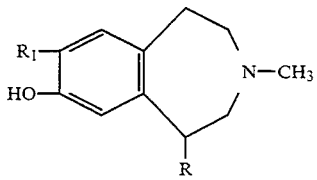

| Compound | R₁ | R | $K_i$, nm D1 | $K_i$, nm D2 | NA = not active Rat CAR (mpk @ 1 h) |
|---|---|---|---|---|---|
| M | Cl | 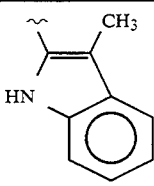 | | | No data |

In the above table, the notation NA means not active at 30 mpk.

Based upon the above data it can be seen that the compounds of the invention have anti-psychotic and anti-depressive activity.

COMPETITIVE INHIBITION ASSAY

Many compounds capable of effecting reproducible physiological changes in neural tissues are believed to operate by binding at one or more receptor sites in in vitro tests, using homogenates of the target organ or structure, are expected to exhibit similar properties when administered in vivo and are, therefore, candidates for continued study as potential therapeutic and/or diagnostic agents.

Binding of a compound to a receptor site, in vitro, is demonstrated by the specificity of binding and the saturability of the available sites. A methodology for characterization of binding and an interpretation of the data are described by Billard et al., *Life Sciences* 35, 1885 (1984) in which the binding of the benzazepine (R)-(+)-8-chloro-2,3,4,5-tetrahydro-3-methyl-5-phenyl-1H-3-benzazepin-7-ol hemimaleate (SCH 23390) to the dopamine D-1 receptor is characterized.

Materials and Methods

Tritiated SCH 23390 and tritiated spiperone (a potent D-2 ligand) were obtained as described in the Billard et al. reference supra and serially diluted in 0.05M Tris buffer, pH 7.4, as required. A compound of the invention is diluted in 0.05M Tris buffer, pH 7.4, as required.

Tissue Preparation

Male Sprague-Dawley rats (200 to 250 g) from Charles River Breeding Laboratories, Mass. were used to obtain brain tissue. The rats were humanely sacrificed and their brains removed and placed on ice. Striatal tissue was excised, pooled, and homogenized (Brinkman Polytron, 10 seconds) in 100 volumes (w/v) of ice cold 50 mM Tris buffer, pH 7.4 (at 25° C.). The homogenate was centrifuged at 20,000×g for 10 minutes. The resultant pellet was rehomogenized in Tris buffer and centrifuged again. The final pellet was resuspended in 50 mM Tris buffer pH 7.4 containing 120 mM NaCl, 5 mM KCa, 1 mM CaCl₂, and 1 mM MgCl₂.

Assay

Polypropylene incubation tubes received 100 μl of the individual test compounds at various concentrations dissolved or suspended in 0.05M Tris, pH 7.4 containing 4 mg/ml methylcellulose, 100 μl of a solution of ³H-SCH 23390 in Tris buffer (final reaction mixture concentration=0.3 nM) or 100 μl of a solution of 3H-spiperone in Tris buffer (final concentration=0.2 nM) and 800 μl of tissue suspension (ca. 3 mg/assay). Tubes were incubated at 37° C. for 15 minutes and rapidly vacuum filtered through Whatman GM/B filters and rinsed 4 times with 4 ml of ice cold 50 mM Tris buffer, pH 7.4. The filters were transferred to scintillation vials, equilibrated with 10 ml of scintillant (Scintosol, Isolab, Inc.) for 16 hours at 25° C. and the radioactivity determined in a liquid scintillation counter. $K_i$ values were determined as described by Billard et al. using the relationship $K_i = IC_{50}/(1+([L]/K_D))$ wherein $IC_{50}$=concentration of test drug necessary to displace 50% of specifically bound ³H-Sch 23390, [L]=concentration of radioligand used in the assay, and $K_D$=dissociation constant.

Results

The inhibition constants ($K_i$) determined from the assays for compounds of the invention are as shown in Table 1 above.

The comparatively small $K_i$ values of these compounds in the competitive binding assay with SCH 23390 indicate that the compounds of formula I bind strongly to the D-1 receptor site. The relatively high $K_i$ values for the D-2 site, for which spiperone is highly selective, indicates that the compounds are not specifically bound to that receptor site.

Based upon the above data it can be seen that the compounds of the invention have the following biological activity: they are useful in the treatment of psychoses, depression, pain, hypertension, schizophrenia and drug dependence.

The antidepressive method of the invention is identified, for example, by test procedures which measure a compound's effect on tetrabenazine (TBZ)-induced ptosis in mice or which measure a compound's effect on muricide activity in rats as discussed below.

ANTIDEPRESSANT POTENTIAL EFFECTS ON TETRABENAZINE (TBZ)-INDUCED PTOSIS IN MICE

Clinically active antidepressant drugs are known to block TBZ-induced ptosis in mice (Psychosomatic Medicine, Nodine and Moyer, Eds., Lea and Febiger, Philadelphia, 1962, pp 683–90). Activity in this test is used to predict anti-depressant activity in man. Activity of compounds of the invention as anti-depressive agents may be demonstrated by this test described just below.

Methods and Materials

Groups of 5 mice are administered test drugs followed 30 minutes later by ip injection of tetrabenazine, 30 mg/kg. Thirty minutes later, the degree of ptosis is evaluated. Percent blockade of each treated group is used to determine $ED_{50}$'s, defined as that dose which prevents ptosis in 50% of mice. $ED_{50}$'s and 95% confidence limits are calculated by probit analysis.

EFFECTS ON MURICIDAL BEHAVIOR IN RATS

Blockade of muricidal (mouse-killing) behavior in rats is used as a measure of evaluating the antidepressant activity of drugs (Int. J. Neuro-pharamacol., 405–11 (1966)).

Methods and Materials

Groups of 5 rats are administered test drug intraperitonially and are tested 30 and 60 minutes later for the presence of muricidal behavior. Percent blockade of each treated group using data obtained at both these time points is calculated and dose-response data are used to determine each $ED_{50}$. $ED_{50}$ is defined as that dose which blocks muricide behavior in 50% of treated rats and is calculated using probit analysis.

The analgesic effect of the compounds of formula I and the method for providing analgesia may be exemplified by the Acetic Acid Writhing Test in Mice described below.

ACETIC ACID WRITHING TEST IN MICE

The blockade of writhing induced by the intraperitoneal injection of acetic acid is an established experimental animal model for the screening of antinociceptive drugs (drugs which prevent the appreciation or transmission of pain sensations). See Hendershot et al., *J. Pharmacol. Exp. Therap.* 125"237. (1959) and Koster et al., *Fed. Proc.* 18:412, (1959).

METHOD AND MATERIALS

Compounds to be tested are dissolved or suspended in aqueous 0.4% methylcellulose vehicle. For oral administration, dosages are prepared for delivery of the selected weight of compound in a total volume of 20 mg/kg of body weight. For subcutaneous or intraperitoneal administration, dosages are prepared for delivery of the selected weight of compound in a volume of 10 ml/kg of body weight.

The test procedure is that described by Hendershot et al., supra, except that acetic acid is substituted for phenylquinone. Groups of five male CF1 mice (20–26 g.) are dosed orally with test drug and injected 15 minutes later with 0.6% aqueous acetic acid (10 mg/kg). The mice are placed in a large observation beaker and the number of writhes for each animal is counted during a 10 minute interval starting 3 minutes after injection of acetic acid. A writhe is defined as a sequence of arching of the back, pelvic rotation and hindlimb extension. Initial screening is performed using a dosage of 20 mg/kg. If this dose affords 50% or greater reduction in the number of writhes compared to the control, the animal is considered to be protected, a dose response curve is developed using a logarithmic sequence of lower doses and an $ED_{50}$ is determined by interpolation.

For preparing pharmaceutical compositions from the compounds of formula I, inert, pharmaceutically acceptable carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it may also be an encapsulating material. In powders, the carrier is a finely divided active compound. In the tablet, the active compound is mixed with a carrier having the necessary binding properties in suitable proportions and compacted to the shape and size desired. The powders and tablets typically contain from 5 to about 70% of the active ingredient dependent upon the potency of the active compound, the size and age of the specific therapy. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and other materials typically used in the pharmaceutical industries. The term "preparation" intended to include the formulation of the active compound with encapsulating material as carrier, providing a capsule in which the active component (with or without other carriers) is surrounded by a carrier, which is thus in association with it. Similarly, cachets are included. Tablets, powders, cachets and capsules can be used as solid dosage forms suitable for oral administration.

For preparation suppositories, a low melting wax such as a mixture of fatty acid glycerides or coca butter is first melted and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example there may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous materials, i.e., natural or synthetic gums, resins, methylcellulose, sodium carboxymethylcellulose and other well known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic aqueous salt solutions, ethanol, glycerine, propylene glycol and the like, as well as mixtures thereof. The solvent utilized will be chosen with regard to the route of administration. For example, liquid preparations containing large amounts of ethanol are not generally suitable for parenteral use.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. A dose of about 0.02 to about 2.0 mg/kg, preferably about 0.02 to about 0.2 mg/kg, may be employed and may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

EXAMPLE 1

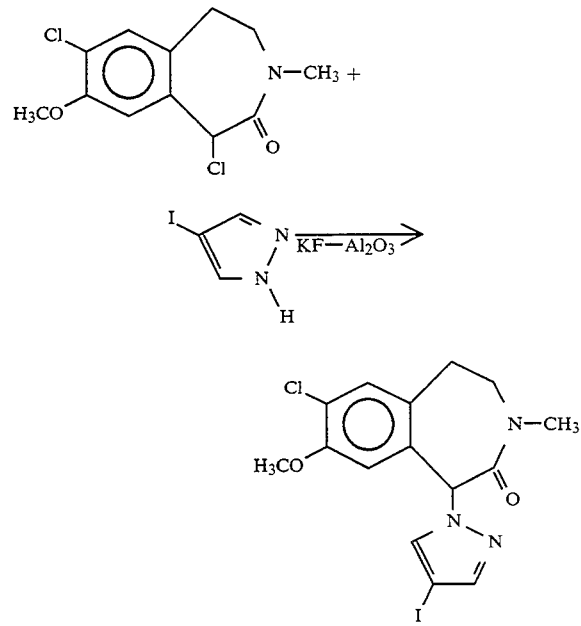

The amide (1.4 g, 5.1 mmol), base (2.06 g, 12.8 mmol), and pyrazole (1.0 g, 5.15 mmol) are placed in a 125 mL round bottom flask, evacuated and purged with argon. Dimethylformamide (DMF) (25 mL) is added and the reaction warmed to ~125°–140° C. After 12–18 hours, cool to room temperature, add water (~200 mL), and filter. Add an additional 100 mL water and transfer to a separatory funnel. Extract with ethyl acetate (EtOAc) (3×100 ml). Wash with water (4×50 mL) and brine (1×50 mL). Dry the ethyl acetate over $Na_2SO_4$, filter and rotovap. Purify the residue by column chromatography using EtOAc as solvent. The starting materials used in this example are either known or may be prepared by known methods.

Physical data for the 2HCl form of the title compound of this example is as follows:

M.P. = 144°–145° C.

NMR (DMSO) δ: 9.80 (1H, s, OH); 7.85 (1H, s); 7.60 (1H, s), 7.15 (1H, s); 6.38 (1H, s); 5.75 (1H, s), 5.72 (1H, d); 3.14 (1H, d); 2.65–3.17 (4H, m); 2.36 (3H, s); 2.10–2.23 (1H, m).

M.S. (FAB-NBA-DMSO) e/m: 278 (100), 280 (33); 209 (63), 211 (30); 210 (58), 212 (22).

The $KF-Al_2O_3$ which is used in the above example is prepared as follows:

10 g of KF were dissolved in 200 mL water. Alumina (15 g) was added and the mixture stirred for ½ hour. Water was removed on the rotovap (~60° C.). The product was dried under vacuum to give a white solid which was the $KF-Al_2O_3$ which was used in the above example.

EXAMPLE 2

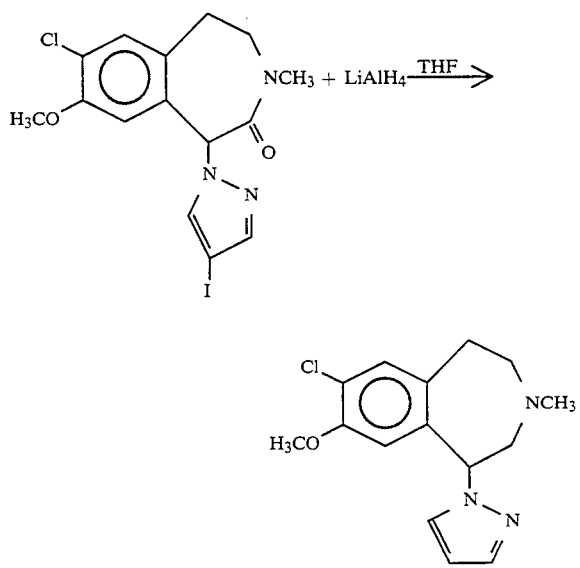

Benzazepine (1.3 g, 3 mmol) was dissolved in tetrahydrofuran (THF) (35 mL) and cooled to 0° C. LiAlH$_4$ (0.34 g, 9 mmol) was added slowly in portions. After 10 minutes the reaction mixture was warmed slowly to 50° C. (~15 minutes). The reaction mixture was stirred at 50° C. for hours, cooled to 0° C. and quenched with water (5 mL), 10% sodium hydroxide (5 mL), and water (5 mL)). After stirring for about ½ hour, the solution was decanted from the flask and extracted with ethyl acetate (3×50 mL). The organic layer was washed with brine (1×25 mL) and dried over $Na_2SO_4$, filter and rotovapped. The residue was purified by column chromatography (5% MeOH/EtOAc).

EXAMPLE 3

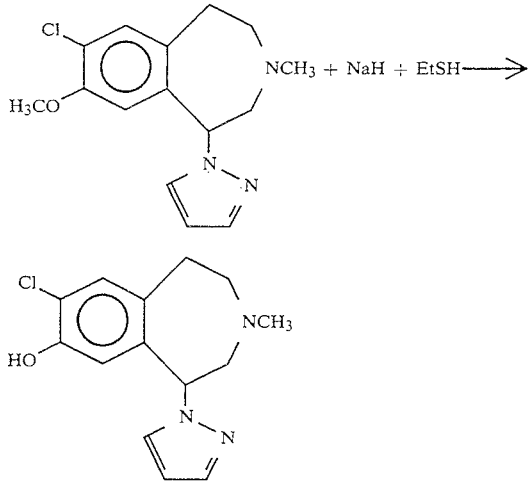

Under cooling in a dry ice/isopropanol bath, add the EtSH (0.64 g) to a mixture of DMF (5 mL) and NAH (0.42 g). After 5 minutes, add a DMF (15 mL) solution of the benzazepine (0.72 g). Warm to 140° C. over a 20 minute period and maintain for 6 hours. Cool to room temperature and adjust pH to 6–7 with acetic acid. Add 15 mL saturated NaHCO$_3$ and rotovap to remove volatiles. Add 100 mL water and extract with ethyl acetate (3×75 mL). Wash with water and brine and dry over Na$_2$SO$_4$. Filter and rotovap. Purify by column chromatography (EtOAc:EtOH, 1:1).

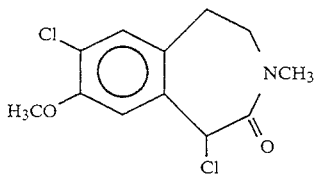

is a starting material used in the preparation of the compounds of the invention. The preparation of this starting material is described in U.S. Pat. No. 5,015,639. See Column 30, Preparation Example 6.

Compounds of the invention are made from this starting material. A representative procedure for preparing compounds of the invention is set forth in the examples just above.

The compounds which are listed below were prepared by processes analogous to those given in examples 1 through 3 above. Physical data for these compounds of the invention along with their structures are as follows:

$C_{19}H_{19}N_2OCl = 326.83$

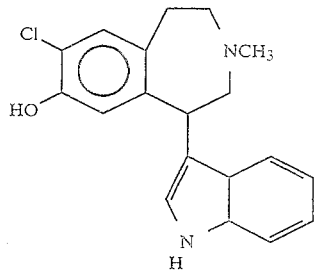

Analysis calculated: C=69.82, H=5.87, N=8.57
founded: C=69.96, H=5.92, N=8.81
FAB-NBA-DMSO, MS m/e 326.90 (100)
N.M.R. DMSO: δ 2.22 (t, 1H), 2.26 (s, 3H), 2.80 (m, 3H), 3.00 (m, 2H), 4.43 (d, 1H), 6.40 (s, 1H), 6.92 (t, 1H), 7.08 (t, 1H), 7.10 (s, 1H), 7.28 (m, 2H), 7.40 (d, 1H), 9.51 (s, 1H), 10.96 (s, 1H).
$C_{20}H_{21}N_2OCl = 340.86$

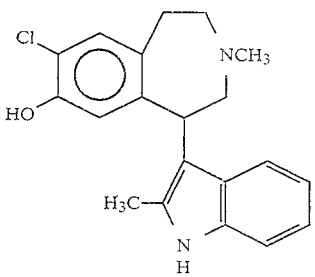

M.P.=268°–269° C.
FAB-NBA-DMSO MS m/e 340.90 (94)
NMR (DMSO): δ 2.07 (t, 1H), 2.26 (s, 3H), 2.27 (s, 3H), 2.75 (m, 2H), 3.01 (m, 2H), 3.15 (t, 1H), 4.15 (d, 1H), 6.30 (s, 1H), 6.90 (t, 3H), 7.00 (t, 1H), 7.01 (s, 1H), 7.28 (t, 2H), 9.45 (s, 1H), 10.90 (s, 1H)
$C_{19}H_{19}N_2OCl = 326.83$

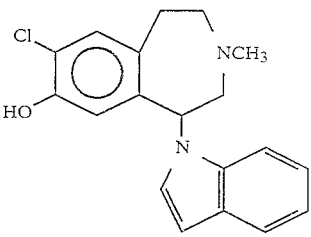

M.P.=237°–239° C.
Analysis calculated: C=69.82, H=5.87, N=8.57
founded: C=69.74, H=5.80, N=8.35
FAB-Thio+HCl - MS m/e 326.90 (100)
NMR (DMSO): δ 2.18 (t, 1H), 2.35 (s, 3H), 2.75 (s, 3H), 2.75 (m, 1H), 2.98 (m, 2H), 3.22 (m, 2H), 5.62 (s, 1H), 5.85 (d, 1H), 6.62 (d, 1H), 7.05 (m, 2H), 7.20 (s, 1H), 7.42 (d, 1H), 7.48 (d, 1H), 7.62 (m, 1H), 9.69 (s, 1H).
$C_{20}H_{22}N_2O = 306.42$

M.P.=240°–242° C.

EI, MS m/e: 306 (76), 248 (61), 190 (100)

NMR (DMSO): δ 2.12 (s, 3H), 2.18 (t, 1H), 2.32 (s, 3H), 2.76 (m, 2H), 2.99 (m, 1H), 3.15 (m, 1H), 3.25 (d, 1H), 5.40 (s, 1H), 5.70 (d, 1H), 6.60 (d, 1H), 6.88 (s, 1H), 7.04 (d, 1H), 7.10 (m, 3H), 7.65 (m, 1H)

$C_{20}H_{21}N_2OCl = 340.81$

M.P.=218°–220° C.

FAB-NBA-DMSO: M.S. m/e 340.90 (100)

NMR (DMSO): δ 2.05 (s, 3H), 2.22 (m, 1H), 2.32 (s, 3H), 2.70 (m, 2H), 3.00 (m, 3H), 4.46 (d, 2H), 6.19 (s, 1H), 6.95 (m, 2H), 7.10 (s, 1H), 7.28 (d, 1H), 7.41 (d, 1H), 9.62 (s, 1H), 10.80 (s, 1H)

$C_{17}H_{21}N_2OCl = 304.83$

M.P.=210°–211° C.

FAB-NBA-DMSO: MS m/e (rel %) 305 (100)

NMR (DMSO): δ 1.80 (s.3H), 2.12 (m, 1H) 2.13 (s, 3H) 2.26 (s, 3H), 2.51 to 3.0 (m, 5H), 4.15 (d, 1H), 5.52 (s, 1H), 6.30 (s, 1H), 7.05 (s, 1H), 9.63 (s, 1H), 10.10 (s, 1H).

$C_{17}H_{21}N_2OCl = 304.83$

M.P.=259°–260° C.

Analysis calculated: C=66.98, H=6.96, N=9.19
found: C=66.31, H=6.94, N=9.22

FAB-NBA-DMSO, MS m/e: 304.9 (100)

NMR (DMSO): δ 1.98 (t, 1H), 1.92 (s, 3H), 2.15 (s, 3H), 2.23 (s, 3H), 2.32 (m, 1H), 2.65 (m, 1H), 2.86 (m, 2H), 2.99 (t, 1H) 3.96 (d, 1H), 5.50 (d, 1H), 6.96 (s, 1H), 7.02 (s, 1H), 9.53 (s, 1H), 10.12 (s, 1H)

$[\alpha]_D^{22} = +20°, C = 1$ EtOH $[\alpha]_D^{22} = -21°, C = 1$ EtOH $[\alpha]_D^{22} = +14.2° C = 0.5$, DMF
Analysis calculated: C = 66.88, H = 6.96, N = 8.19
found: C = 66.08, H = 6.88, N = 8.93

[α]$_D^{22}$ = −10°, C = 0.5, DMF
Analysis calculated: C = 66.98, H = 6.96, N = 9.19
found: C = 66.27, H = 6.89, N = 9.04

$C_{18}H_{23}N_2OCl = 318.86$

M.P. = 234–236° C.
Analysis calculated: C=67.80, H=7.29, N=8.78
found: C=67.58, H=7.25, N=8.65
MS m/e 318.9
NMR (DMSO): δ 1.97 (s, 3H), 1.99 (m, 1H), 2.15 (s, 3H), 2.21 (s, 3H), 2.32 (m, 1H), 2.87 (m, 1H), 2.85 (m, 2H), 3.02 (m, 1H), 3.30 (s, 3H), 4.01 (d, 1H), 5.60 (s, 1H), 6.45 (s, 1H), 7.03 (s, 1H), 9.50 (s, 1H)
MS m/e (rel %) FAB-NBA-DMSO: 318.9 (100), 195 (75)

$C_{16}H_{19}N_2OCl = 290.80$

M.P. = 254–255° C.
Analysis calculated: C=66.08, H=6.60, N=9.63
found: C=65.62, H=6.60, N=9.49
NMR δ 2.04 (t, 1H), 2.27(s, 3H), (s, 3H), 2.42 (s, 3H), 2.70 (m, 1H), 2.90 (m, 1H), 3.12 (m, 2H), 3.28 (s, 3H), 4.24 (s, 1H), 5.88 (m, 1H), 5.95 (s, 1H), 6.03 (m, 1H), 6.72 (m, 1H), 7.10 (s, 1H), 9.65 (s, 1H)
FAB-NBA-DMSO MS m/e (rel %): 290 (67), 219 (27)

$C_{16}H_{19}N_2OCl = 290.80$

M.P. = 190–192° C.
NMR (DMSO): δ 2.20 (t, 1H), 2.22 (s, 3H), 2.55–2.90 (m, 5H), 4.02 (d, 1H), 5.80 (t, 1H), 6.46 (t, 1H), 6.55 (s, 1H), 6.65 (t, 1H), 7.01 (s, 1H), 8.72 (s, 1H)
FAB-NBA-DMSO, MS m/e (rel %): 290 (100), 219 (35), 195 (35)

We claim:

1. A compound of the formula:

or a pharmaceutically acceptable salt thereof,
wherein Ar is selected from the group consisting of and R, $R_1$, $R_2$ and $R_3$ are each independently hydrogen or lower alkyl with the proviso that when Ar is $R_1$ and $R_2$ cannot both be hydrogen;
X is hydrogen, halogen, lower alkyl or —$CF_3$; and
Y is —OR, —OH,

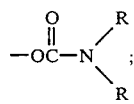

wherein each R is independently as described above.

2. A compound according to claim 1 wherein X is halo, Y is hydroxy, Ar is substituted pyrrolyl and each R, $R_1$, $R_2$ and $R_3$ is independently hydrogen or methyl.

3. A compound of claim 1 wherein X is chloro.

4. A compound of claim 3 wherein Y is hydroxy, R is methyl and Ar is

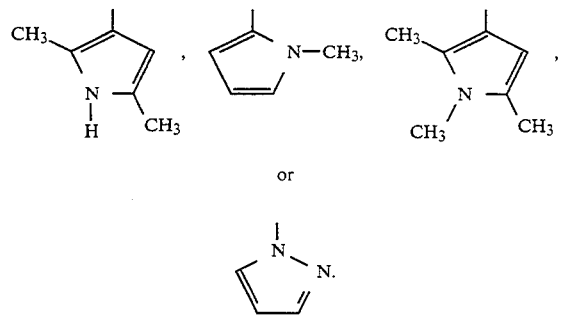

5. A compound according to claim 1

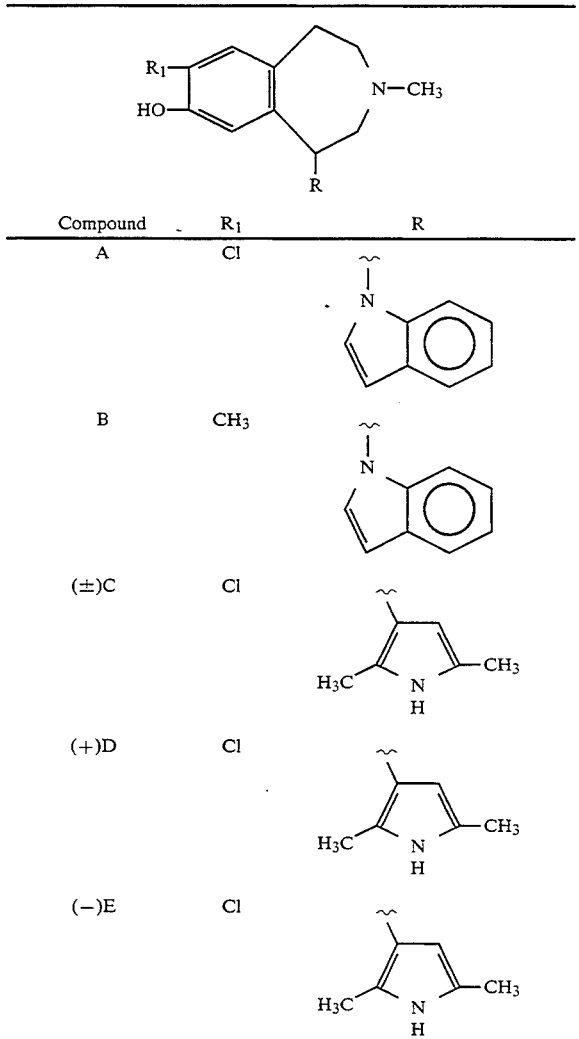

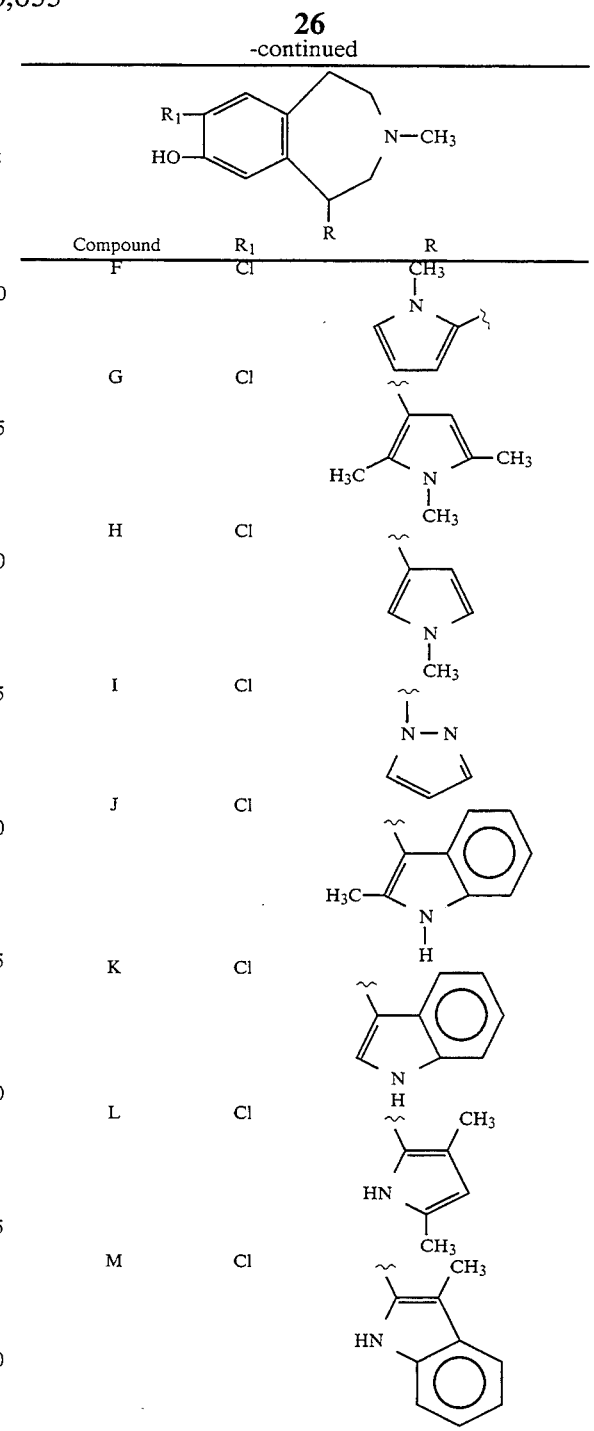

or a pharmaceutically acceptable salt thereof.

6. The compound according to claim 1

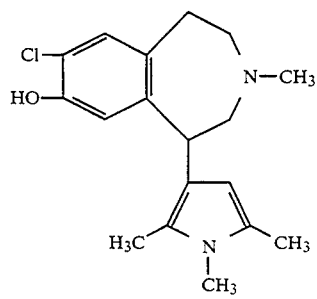

or a pharmaceutically acceptable salt thereof.

* * * * *